US010105288B1

(12) United States Patent
Nosrati et al.

(10) Patent No.: US 10,105,288 B1
(45) Date of Patent: Oct. 23, 2018

(54) SMART MEDICATION ADHERENCE REFRIGERATION TRAY (SMART)

(71) Applicants: Farhad David Nosrati, Encino, CA (US); Daniel Gershoni, Weston, FL (US)

(72) Inventors: Farhad David Nosrati, Encino, CA (US); Daniel Gershoni, Weston, FL (US)

(*) Notice: Subject to any disclaimer, the term of this patent is extended or adjusted under 35 U.S.C. 154(b) by 0 days.

(21) Appl. No.: 15/681,400

(22) Filed: Aug. 20, 2017

(51) Int. Cl.
*A61J 7/04* (2006.01)
*A61J 7/00* (2006.01)
(Continued)

(52) U.S. Cl.
CPC ........... *A61J 7/0481* (2013.01); *A61J 7/0069* (2013.01); *A61J 7/0418* (2015.05); *A61J 7/0436* (2015.05);
(Continued)

(58) Field of Classification Search
CPC .. A61K 2300/00; A61K 31/255; A61K 31/35; A61K 31/357; A61K 31/42; A61K 31/423; A61K 31/7024; A61K 31/137; A61K 45/06; A61K 31/5375; A61K 31/14; A61K 31/221; A61K 31/4748; A61K 31/51; A61K 31/685; A61K 33/06; A61K 31/12; A61K 31/135; A61K 35/04; A61K 9/0014; A61K 31/205; A61K 31/426; A61K 31/465; A61K 38/21; A61K 38/212; A61K 9/0031; A61K 9/0034; A61K 31/415; A61K 31/496; A61K 31/519; A61K 31/5415; A61K 31/551; A61K 31/5513; A61K 31/554; A61K 31/00; A61K 31/34; A61K 31/7068; G07F 17/0092; G07F 9/026; G07F 11/165; G07F 11/44; G07F 11/002; G07F 9/006; G07F 11/16; G07F 11/28; G07F 11/30; G06Q 50/22; G06Q 50/24; G06Q 10/0639; G06F 19/3462; G06F 19/327; G06F 19/18; G06F 19/325; G06F 19/326; G06F 19/22; G06F 19/322; G06F 19/328; G06F 19/3418; G06F 19/3443;
(Continued)

(56) References Cited

U.S. PATENT DOCUMENTS 5,863,451 A 1/1999 Buhler
6,294,999 B1 * 9/2001 Yarin .................... A61J 7/0481
340/573.1

(Continued)

*Primary Examiner* — Daniel Previl

(57) ABSTRACT

A Smart Medication Adherence Refrigeration Tray (SMART) along with method of use to assist with self-management of medication treatment by patients. The SMART medication tray accepts a plurality of medication filled containers of various sizes along with individual storage compartments for each container. Each medication storage compartment uses an embedded scale mechanism to monitor the amount of medication being taken by the patient and to assist with the medication adherence compliance. A series of optical sensors are utilized to detect when medication bottles are placed on the storage compartment as well as when they are being removed. Medication tray utilizes wireless technology to interactively communicate with outside computing devices to receive medication prescription and assist with the adherence process.

36 Claims, 11 Drawing Sheets

(51) Int. Cl.
*G06F 19/00* (2018.01)
*G06Q 10/10* (2012.01)
*G16H 15/00* (2018.01)
*G16H 10/60* (2018.01)

(52) U.S. Cl.
CPC ....... *G06F 19/3456* (2013.01); *A61J 2200/30* (2013.01); *A61J 2200/44* (2013.01); *A61J 2200/74* (2013.01); *A61J 2205/10* (2013.01); *A61J 2205/20* (2013.01); *A61J 2205/70* (2013.01); *G06F 19/3418* (2013.01); *G06Q 10/109* (2013.01); *G16H 10/60* (2018.01); *G16H 15/00* (2018.01)

(58) Field of Classification Search
CPC . G06F 19/3456; G06F 19/3493; B65B 57/00; B65G 1/06; A61B 10/007; A61B 5/002; A61B 5/0022; A61B 5/0809; A61B 5/145; A61B 5/14507; A61B 5/16; A61B 5/201; A61B 5/208; A61B 5/4878; A61N 1/3627; C12Q 1/6883; C12Q 2600/106; C12Q 2600/118; C12Q 2600/156; C12Q 2600/158; C12Q 2600/172; C12Q 1/68; C12Q 1/6825; C12Q 1/6827; C12Q 2563/155; C12Q 2563/185; C12Q 2565/632; G01N 2800/325; G01N 21/64; G01N 21/65; A01K 39/02; A61F 5/003; A61F 5/0036; C07D 217/12; C07D 285/28; C40B 30/02; G01G 17/00; G01G 19/384; G09F 3/00; G16H 10/65; G16H 20/13; G16H 40/20; Y10S 514/863; A61J 2200/30; A61J 2205/10; A61J 2205/30; A61J 2205/60; A61J 2205/20; A61J 1/10; A61J 1/1462; A61J 1/1468; A61J 1/1487; A61J 2200/42; A61J 2200/72; A61J 2205/50; A61J 7/0084; A61J 2205/70
USPC ..... 340/573.1, 666, 691.1, 691.6, 10.1, 505, 340/5.8, 5.81, 5.92, 326, 572.1–572.9
See application file for complete search history.

(56) References Cited

U.S. PATENT DOCUMENTS

| | | | |
|---|---|---|---|
| 9,387,154 B2 | 7/2016 | Aggarwal et al. | |
| 2004/0015132 A1* | 1/2004 | Brown | A61B 5/0002 604/131 |
| 2009/0301925 A1* | 12/2009 | Alloro | G06F 19/3462 206/534 |
| 2013/0222135 A1* | 8/2013 | Stein | A61J 7/0409 340/540 |
| 2015/0272825 A1* | 10/2015 | Lim | A61J 1/03 340/5.2 |
| 2016/0074283 A1* | 3/2016 | Aggarwal | A61J 7/04 206/534 |

\* cited by examiner

SMART MEDICATION ADHERENCE REFRIGERATION TRAY (SMART)

CROSS-REFERENCE TO RELATED APPLICATIONS

This application takes priority from provisional application Ser. No. 62/378,826 filed on Aug. 24, 2016.

BACKGROUND OF INVENTION

1. Field of the Invention

The present invention, Smart Medication Adherence Refrigeration Tray (SMART), relates to the technical field of health monitoring, and, more specifically, medication adherence monitoring and compliance. The present invention is a wireless smart medication tray and a method to assist with self-management of medication treatment by patients. The SMART medication tray accepts a plurality of medication containers of various sizes and types and provides an individual storage compartment for each container. Each medication storage compartment uses an embedded scale mechanism to monitor the amount of medication being taken by the patient and to assist with the medication adherence compliance.

2. Description of Prior Art

A variety of products and techniques for reminding patients to take their medications, as prescribed, are known. Patients frequently exhibit poor patient compliance in properly following through a particular drug regimen. Some compliance intervention systems offered by healthcare providers are designed to remind the patient to take the medication and alert a remote caregiver if the patient does not comply with taking the medication as prescribed. Some of these compliance intervention systems include sensors/reminders in the home, a network connection, and outbound messaging to a caregiver or even back to the patient. A problem with these is that although they remind someone that a medication dose is due, they do not ensure that a dose was taken or provide evidence that a dose was taken. The present invention overcomes these deficiencies.

Another issue arises with monitoring liquid medication, such as syrups, solutions and injectable medications. Some of the prior art manage liquid medicine by adding a sensing mechanism to the removable cap of the container to alert when the cap is removed. A significant problem with this approach however, is that there currently is no mechanism in place to determine what dosage amount of the medication if any was actually taken by the patient. These types of notifications prove to be of very limited assistance with the medication adherence process. The present invention overcomes this deficiency.

Additionally, many of these liquid medications require refrigeration. There are refrigerator trays that organize and store medication containers in a refrigerated environment. While these trays help segregate medication from the other items in a refrigerator, a significant problem is that they have no ability of themselves to automatically assist with ensuring the correct dosage of liquid medicine is being taken, therefore cannot play an effective role in the medication adherence process. The present invention overcomes this deficiency.

There are some medications that come in loose, meaning not encased in a capsule or compacted into a pill. These medications rely on the patient to measure out the correct amount of medication for each and every dose. Such medications are usually in powder form. Significant problems lie in relying on the patient to remember both the correct dosage and the weighing out of proper dosage. As discussed above, it is of very little value for medication adherence purposes to rely on the patient to remember to timely take medications, let alone to weigh out the proper dosage. The present invention overcomes these deficiencies.

The present invention improves prior systems and overcomes the prior systems' deficiencies.

SUMMARY OF THE INVENTION

In accordance with one aspect of the invention, a Smart Medication Adherence Refrigeration Tray (SMART) is a medication adherence monitoring and assistance apparatus comprised of a wireless smart medication tray along with a method of use to assist with self-management of medication treatment by patients. The present invention includes a tray that accepts a plurality of medication filled containers of various sizes along with an individual storage compartment for each container. Each medication storage compartment uses an embedded scale mechanism to monitor the amount of medication being taken by the patient and to assist with the medication adherence compliance. Also included are a series of optical photo sensors to detect when medication bottles are placed on the storage compartment as well as when they are being removed. The medication tray of the present invention utilizes wireless technology to interactively communicate with outside computing devices to receive medication prescription and assist with the patient's medication program's process. In another aspect, the present invention further relates to a medication tray accommodating medication containers requiring refrigeration such as liquid medicine, syrups, solutions and those being injectable.

Adherence to a medication program is not always easy and assistance and monitoring of that program is not always a simple binary "Yes/No" or "Pass/No Pass" process as practiced by most prior art solutions. The present invention features an interactive and a continuous analog monitoring process. Prior art solutions all take the "binary" approach to this process. They do so, by either relying on feedback from the patient on whether or not the medication was taken as prescribed, or by relying on various "alert" systems and "binary" input sensors to provide feedback as to whether or not the medication was taken, and when it was taken. By way of example, a number of prior art solutions have placed various sensing mechanisms to detect when a medication container has been removed from the storage-shelf. Another example is the use of a sensor embedded within the container cap to determine if and when the container was opened. In stark contrast, the present invention is unique and novel in that it utilizes embedded weight scales in each storage compartment to continuously measure and monitor the weight of each individual medication container and provide a comprehensive "Analog" feedback on the medication adherence compliance by the patient.

Another feature of the present invention is a liquid, aerosol, solid, and powder medication management. The present invention utilizes a series of weight scales to continuously measure and monitor the weight of each individual medication container. The medication prescription details including the medication schedule and dosages are uploaded into the present invention. The weight of each medication container is initially measured and recorded using the above mentioned scales. A sensor is utilized to detect when a medication container is removed from its storage compartment, and then is placed back in the container. The weight of the medication container is constantly measured prior to its removal and upon its return to the SMART medication tray to determine if any medication was used from that container, and if so, the dosage amount that was used to ensure the patient is adhering with the prescribed medication usage.

Another feature of the present invention is a medication monitoring feature. The present invention is novel in the area of being able to provide medication adherence monitoring for the medications that require refrigeration. Utilizing various sizes of storage compartments for the medication containers and the benefit of wireless communication connectivity including to but not limited to Bluetooth, WiFi, 2G and 3G, the present invention helps provide medication continuous monitoring at all times, even when stored inside the refrigerator or any refrigeration compartment or device.

Another feature of the present invention is an audible alert system. Utilizing the above mentioned weight scales along with a built-in audible alarm system, the present invention is novel in that it can continuously monitor the amount of medication being stored in each medication container and notify the patient and/or the caregiver of the status of the medication containers with low or empty medication contents. This interactive mechanism can significantly improve and facilitate the medication adherence compliance.

Another feature of the present invention is an early dose detection feature. Yet another unique benefit of the present invention is the utilization of its built-in sensors and weight scales to help detect when the patient has taken an early does of one or more medications and alert the patient as well as the remotely located monitors and caregivers of the early dosage occurrence.

The innovation of the present invention further includes a series of unique and novel features to assist with and help facilitate the medication adherence monitoring process which include but are not limited to the following:

A unique and novel medication tray. This novel medication tray continuously tracking the various amount of medicine being removed from each medication container.

A unique and novel series of storage compartments. The present invention further utilizes a number of storage compartments capable of accommodating various size medication containers.

A unique and novel optical sensor. Each of the above mentioned storage compartments may further include an optical sensor to help detect when medication containers are being removed from the storage compartment as well as when the containers are placed back in their corresponding storage compartment.

The unique and novel employment of weight scales. Each of the above mentioned storage compartments may further include a scale for measuring various medication dosages including but not limited to liquid medicine, syrups, solutions and injectables.

The present invention utilizes a display unit. A display unit is utilized to indicate various information regarding each medication container including but not limited to the container's initial weight, the amount of medication taken out at each interval as well as the remaining medication left in the container. Furthermore, various pre-recorded instructional messages and videos along images of medication container can be displayed.

The present invention further provides for color-coded keys. A color-coded tagging mechanism is provided to uniquely identify each medication container and its correspond storage compartment. Furthermore, the display unit also utilizes the same color-code system to indicate various information regarding each medication container.

The present invention also provides for proximity light sensors. The present invention may further include sensing mechanism to detect a user approaching the device and illuminate a light panel when they are within close proximity of the device.

The present invention may further include biometrics sensors such as fingerprint and retina scanners for secure access to and programming of the device.

The present invention may further include a camera, microphone and speaker set to allow live audio and video communication with care givers and remote call center operators.

The present invention may further include sensing mechanism to illuminate a light panel when the device is touched by a user.

The present invention further provides for wireless technologies including but not limited to Bluetooth, WiFi, 2G and 3G communications to interactively communicate with outside computing devices.

The present invention may further include a built-in thermometer to monitor the ambient temperature where the medication tray is being kept. In addition, user contact points are provided to assist with measuring body temperature. The display unit provides the temperature reading locally, while a wireless communication module will transmit that information to remote operators and caregivers.

The present invention further provides for a unique and novel low medication indicator. The present invention can further utilize its embedded weight scales to notify the patient of the status of the medication containers with low medication content.

The present invention further features an alarm mechanism. The present invention may include an audible alarm to alert the patient in the event that one or more medication has not been taken as scheduled.

The present invention may further include a built-in rechargeable battery with battery-charge status light indicators.

The present invention may also be equipped with GPS locator technology to assist the remote operators and caregivers as to the location of the SMART Medication Tray.

It is an object of the present invention to have a medication-adherence assistance apparatus to provide assistance maintaining a medication regimen, to remind a user to take medication, to provide information to users, operators, and caregivers, and to track medication compliance, said users, operators, and caregivers, and the user having at least one medication container containing a medication and the medication having a dosage and a schedule, the apparatus comprising: a processor; a memory; a wireless transceiver, wherein said wireless transceiver may include a multiplicity of functions, including downloading and providing access to a medication schedule and medication dosage; a speaker; an interface, the interface further comprising a display and at least one input device; at least one storage compartment for placing and storing the medication container, the at least one storage compartment having a base, and the at least one storage compartment being associated with a single medication container, a scale mechanism, a sensor mechanism, a housing, said housing configured to contain the processor, the memory, the wireless transceiver, the display, the speaker, the sensor mechanism, and the at least one storage compartment; wherein said wireless transceiver, said scale and said sensor reside on the base of the storage compartment and are in electronic communication with each other such that they detect when medication has been removed from the base as well as when medication has been returned to the base, notify remote operators and caregivers when medication is dispensed, detect the weight of each medication container at all times and log the weight information prior to each time a bottle is removed and immediately after it is returned, calculate the amount of medication being used each time, providing notifications to a user via the interface display and the speaker, and notify remote operators and caregivers; a dispense schedule, wherein said dispense schedule is downloaded into the device, remotely or locally, and wherein said dispense schedule further is capable of receiving the dosage of the medication; a monitoring protocol, wherein said monitoring protocol monitors the downloaded medication schedule and wirelessly notifies local operators and remote operators and caregivers of when the medication container has been removed from and returned to the storage compartment of the tray, and the amount of medication that was used; and wherein the device, programs, and protocols are capable of being programmed with the medication dosage and usage schedule for one or more medication containers.

It is another object of the present invention that the present invention medication-adherence assistance apparatus further comprises a microphone.

It is another object of the present invention that the present invention medication-adherence assistance apparatus wherein the at least one storage compartment is removable from the housing.

It is another object of the present invention that the present invention medication-adherence assistance apparatus further comprises a time out alert, wherein the apparatus, upon sensing when a storage compartment has been removed from the housing, begins a timer of a predetermined length of time, at the end of which the interface display and speaker provide notifications to the user to return the storage compartment to the housing.

It is another object of the present invention that the present invention medication-adherence assistance apparatus further comprises a time out alert, wherein the apparatus, upon sensing when a storage compartment has been removed from the housing, begins a timer of a predetermined length of time, at the end of which the interface display and speaker provide notifications to remote operators and care givers that the storage compartment has not been returned to the housing.

It is another object of the present invention that the present invention medication-adherence assistance apparatus further comprises a color-coded system, wherein the storage compartment is designated a color and the programs, protocols and display unit further record and report the color coding in association with the medication and other reporting functions, and whereby each medication container is matched with its storage compartment in the housing and shown on the interface.

It is another object of the present invention that the color-coded system further comprises a specific location for each individual color-coded storage compartment and a sensor that can detect if a color-coded storage compartment has or has not been returned to its color-coded location, and an alert to notify the user to return the color-coded storage compartment to its designated location.

It is another object of the present invention that the present invention medication-adherence assistance apparatus further comprises a cooling mechanism and housing that encompasses the storage compartment and its associated medication container thereby providing that medications that require refrigeration are kept cool while outside of a refrigerator.

It is another object of the present invention that the present invention medication-adherence assistance apparatus wherein the at least one storage compartment is removable and further comprises a wireless connectivity link to the main medication housing.

It is another object of the present invention that the present invention medication-adherence assistance apparatus further comprises a GPS locator to notify remote operators and care givers via wireless communication of the location of the device.

It is another object of the present invention that the present invention medication-adherence assistance apparatus further comprises a bar-code scanner to scan in medication containers.

It is another object of the present invention that the present invention medication-adherence assistance apparatus an alarm to remind the user to take medication and to remind the user to return the storage compartment to a refrigerator.

It is another object of the present invention that the present invention medication-adherence assistance apparatus further comprises a self-contained cooling compartment.

It is another object of the present invention that the present invention medication-adherence assistance apparatus further comprises a secure mobile access, wherein the apparatus is paired to a wireless device and notifies the caregiver and user of the user's medication-adherence status.

It is another object of the present invention that the present invention medication-adherence assistance apparatus storage compartment is a removable stand-alone storage compartment configured to detect when a medication bottle is removed from and returned to a storage container, to log that information, to compare the information with pre-stored medication usage schedule, and to report that information via wireless communication to the apparatus and to an operator user.

It is another object of the present invention that the present invention medication-adherence assistance apparatus removable stand-alone storage compartment is further configured to determine the weight of the medication container before it is removed from container and after when it is returned, to log that information, to compare the information with pre-stored medication usage schedule, and to report that information via wireless communication to the apparatus and to an operator user.

It is another object of the present invention that the present invention medication-adherence assistance apparatus, wherein the removable stand-alone storage compartments further comprises a GPS locator device configured to monitor the location of the medication container and to notify remote operators and caregivers via wireless communication of the location of the device.

It is another object of the present invention that the present invention medication-adherence assistance apparatus housing is generally a tray.

It is another object of the present invention that the present invention medication-adherence assistance apparatus operates to provide assistance maintaining a medication regimen, to remind a user to take medication, to provide information to users, operators, and caregivers, and to track medication compliance, said users, operators, and caregivers, and the user having at least one medication container containing a medication and the medication having a dosage and a schedule, the method comprising the steps of: entering a new medication container's data, at least including, name of medication, dosage, and when medication should be taken and storing this information; placing the medication container in a storage compartment; weighing the medication container and logging that data; notifying a caregiver remotely that a medication container was placed in a storage compartment; sensing when a medication container is removed from the storage compartment; sensing when a medication container is returned to the storage compartment; weighing the medication container and logging the data; comparing the returned weight of the medication container to the previously logged weight and calculating the amount of medication used; reporting to the caregiver remotely the amount of medication used; comparing the amount of medication used to the previously stored required dosage information; determining if the amount of medication used was in compliance with the required dosage; and notifying the caregiver whether or not the amount of medication taken was in compliance with the required dosage.

It is another object of the present invention that the present invention medication-adherence assistance apparatus further comprises the steps of a color-coding matching protocol comprising the steps of: color-coding the storage compartments; color-coding each storage compartment's designated location in the housing tray; sensing whether the color-coded storage compartment is residing on its designated location; notifying the user when the color-coded storage compartment is not residing on its designated location; and continuing the notification until the color-coded storage compartment is placed in its designated location.

It is another object of the present invention that the present invention medication-adherence assistance apparatus further comprises the steps of a color-coded notification protocol comprising the steps of: affixing a color-coded tag on the medication container; placing the tagged medication container in a storage compartment having the same color as the tag; and displaying the color on a user interface when referencing the medication.

It is another object of the present invention that the present invention medication-adherence assistance apparatus further comprises the steps of a GPS locator protocol comprising the steps of: adding a GPS locator to the housing tray; and accessing the GPS locator, for a user to find a missing tray and for a remote caregiver to assure that tray is with the user and within proximity to its hub.

It is another object of the present invention that the present invention medication-adherence assistance apparatus further comprises the steps of: sensing how long a storage compartment has been away from a refrigerator; and notifying the user to return the storage compartment to the refrigerator.

It is another object of the present invention that the present invention medication-adherence assistance apparatus further comprises the steps of a mobile device security protocol comprising the steps of: waiting and sensing that it is the appropriate time for medication to be dispensed; sensing whether a mobile security device is within connectivity range; notifying the user that it is time to take medication, if no mobile security device is detected nearby; returning to step z until a mobile security device is detected; detecting whether the mobile security device is enabled; notifying the user of the medication adherence status; and returning to the beginning of this loop.

The method of claim 19, further comprising the steps of a mobile security adherence protocol comprising the steps of: notifying a remote caregiver that it is time to take medication, if no mobile security device is detected nearby; and notifying a remote caregiver of the medication adherence status.

It is another object of the present invention that the present invention medication-adherence assistance apparatus to provide assistance maintaining a medication regimen, to remind a user to take medication, to provide information to users, operators, and caregivers, and to track medication compliance, said users, operators, and caregivers, and the user having at least one medication container containing a medication and the medication having a dosage and a schedule, and further provided with a storage container and a display unit, the method comprising the steps of: receiving, uploading, updating and saving medication information, including name of medication, dosage, and dosage schedule; performing self-diagnostics; weighing the medication container and recording the weight; sensing whether the medication container has been removed from a storage container; logging the time stamp of the removal of a medication container from a storage container, starting a timer, and notifying a caregiver; sensing whether the medication container has been returned to the storage container; logging the time stamp or the return of the medication container to the storage tray, stopping the timer, and notifying a caregiver; weighing and logging the weight of the returned medication container and the duration of time the medication container was away from the storage container; perform medication adherence analysis, said adherence analysis further comprising the steps of comparing the weight of the medication used to the amount of the previously entered dosage, comparing the time stamp when the medication was removed to the previously entered dosage schedule; and reporting the results to the user.

It is another object of the present invention that the present invention medication-adherence assistance apparatus further comprises the step of reporting the results to a remote caregiver.

It is another object of the present invention that the present invention medication-adherence assistance apparatus further comprises the step of sending the notifications via a display unit.

It is another object of the present invention that the present invention medication-adherence assistance apparatus further comprises the step of sending the notifications via wireless devices.

It is another object of the present invention that the present invention medication-adherence assistance apparatus further comprises the step of associating the medication container with a particular storage compartment.

It is another object of the present invention that the present invention medication-adherence assistance apparatus further comprises the steps of a color-coding matching protocol comprising the steps of: color-coding the storage compartments; color-coding each storage compartment's designated location in the housing tray; sensing whether the color-coded storage compartment is residing on its designated location; notifying the user when the color-coded storage compartment is not residing on its designated location; and continuing the notification until the color-coded storage compartment is placed in its designated location.

It is another object of the present invention that the present invention medication-adherence assistance apparatus further comprises the steps of a color-coded notification protocol comprising the steps of: affixing a color-coded tag on the medication container; placing the tagged medication container in a storage compartment having the same color as the tag; and displaying the color on a user interface when referencing the medication.

It is another object of the present invention that the present invention medication-adherence assistance apparatus further comprises a the steps of a GPS locator protocol comprising the steps of: adding a GPS locator to the housing tray; and accessing the GPS locator and locating a missing tray, and assuring a remote caregiver that tray is with the user and within proximity to its hub.

It is another object of the present invention that the present invention medication-adherence assistance apparatus further comprises the steps of: sensing how long a storage compartment has been away from a refrigerator; and notifying the user to return the storage compartment to the refrigerator.

It is another object of the present invention that the present invention medication-adherence assistance apparatus further comprises the steps of a mobile device security protocol comprising the steps of: waiting and sensing that it is the appropriate time for medication to be dispensed; sensing whether a mobile security device is within connectivity range; notifying the user that it is time to take medication, if no mobile security device is detected nearby; returning to step z until a mobile security device is detected; detecting whether the mobile security device is enabled; notifying the user of the medication adherence status; and returning to the beginning of this loop.

It is another object of the present invention that the present invention medication-adherence assistance apparatus further comprises the steps of a mobile security adherence protocol comprising the steps of: notifying a remote caregiver that it is time to take medication, if no mobile security device is detected nearby; and notifying a remote caregiver of the medication adherence status.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

It should be noted that references to "an," "one," or "various" embodiments in this disclosure are not necessarily to the same embodiment, and such references contemplate more than one embodiment.

Figure 1:
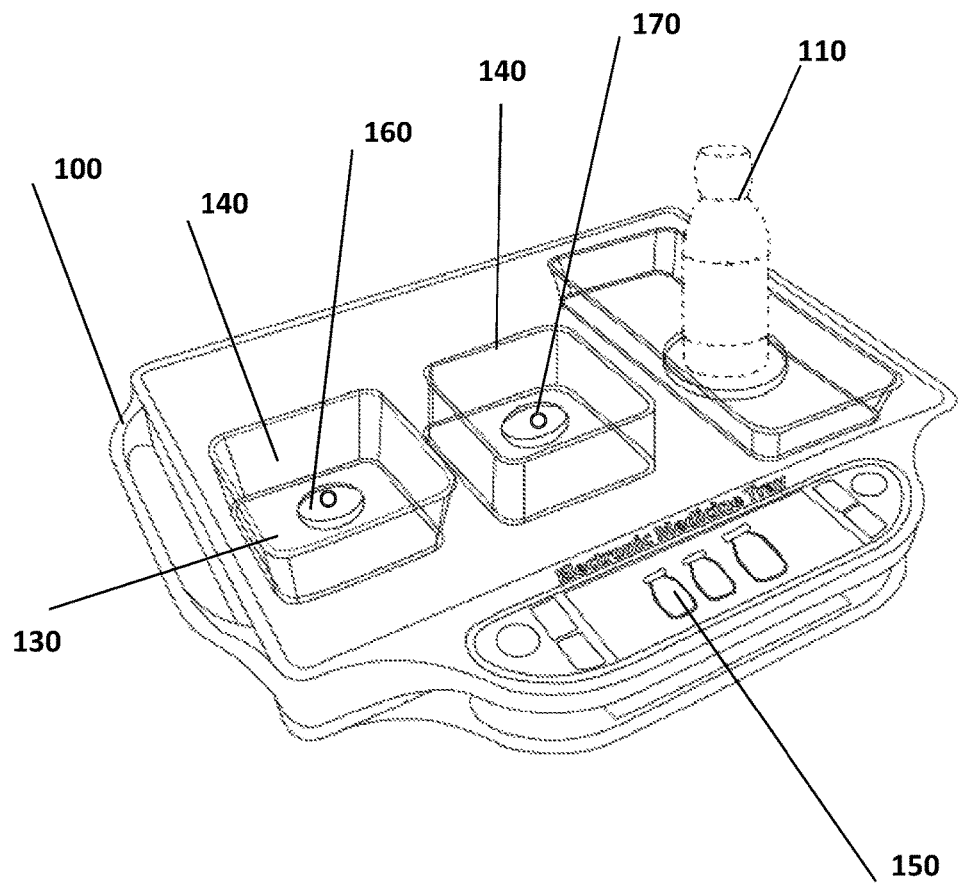
FIG. 1 is a preferred embodiment of the present invention Smart Medication Adherence Refrigeration Tray (SMART)

The present invention disclosed herein and illustrated in FIGS. 1 through 3 is Smart Medication Adherence Tray configured to provide a system for tracking medication compliance.

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized current Good Manufacturing Practice guidelines.

As used herein the term "Computing Device"" includes a desktop, laptop or tablet computer, as well as a mobile device.

"Software Application" means all the computer software that causes a computer to perform useful tasks beyond the running of the computer itself.

Referring now to FIG. 1, there is illustrated a preferred embodiment of the present invention 1000. A plurality of storage compartments 140 provide storage area for various size medication containers 110. Each storage compartment 140 at least has a base 130. The base 130 of each of the storage compartments 140 comprises of a scale 160 that provides weight measurement of the medication container 110 being stored in that compartment 140. The base unit 130 of each of the storage compartment 140 further comprises of an optical sensor 170 that can detect when a medication container 110 is placed in the storage compartment 140 and when it is removed from it. Each storage compartment 140 may further be color-coded to assist the user in locating and identifying the correct medication container 110. The storage compartments 140 reside on the housing 100 which preferably has a tray-like design.

Medication containers 110 are placed in the storage compartments 140 of the medication tray 100. The medication containers can be bottles, tabs, vials, syringes and the like. Additionally, medication containers 110, or the storage containers 140, may be organized by containing all the medication for a given time of day, such as having one container 110, or storage container 140, have all the morning pills, another having all the afternoon medication, another having all the evening pills, and so on.

Each medication storage compartment 140 includes a weight scale 160 used to measure and monitor the weight of the medication being stored in that storage compartment 140. Additionally, each weight scale 160 may further include a sensor unit 170 to indicate when medication containers 110 have been placed into and removed from the storage compartment 140. Utilizing the weight scale 160 and the sensor 170 reading, the display unit 150 will show the medication amount present in each medication bottle 110.

The display unit 150 shows the status of each medication container 110. The display unit 150 may further display matching color-code key for each container 110 being displayed to further to assist with locating the proper container 110.

Figure 2A:
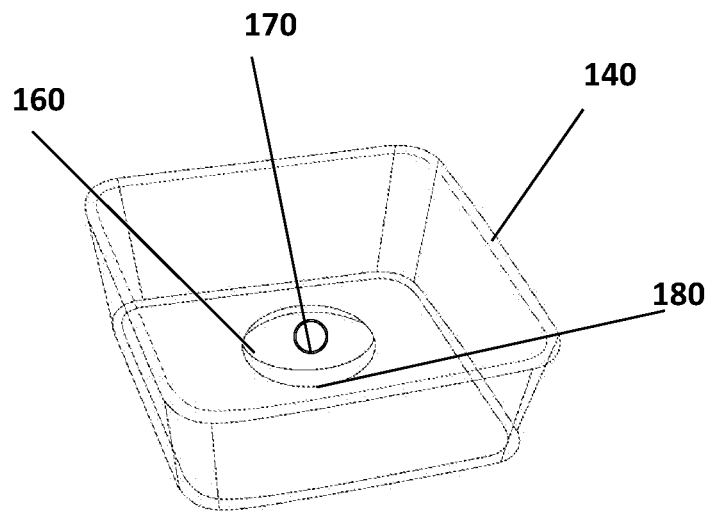
FIG. 2A is a detail of a medication compartment of the present invention.
Figure 2B:
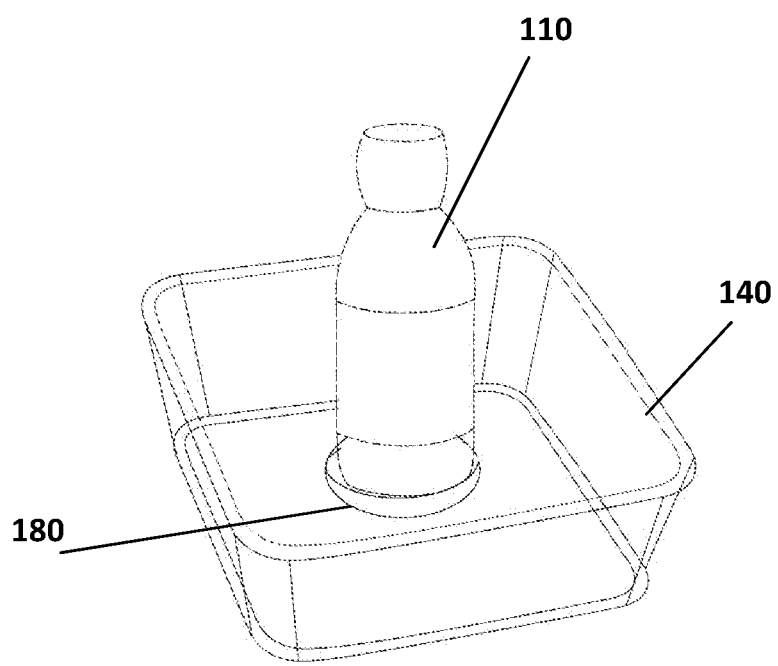
FIG. 2B is a detail of a medication compartment of the present invention shown in use with medication container.

Referring now to FIGS. 2A and 2B, there is shown a detail of the medication storage compartment 140. The storage compartment 140 can be removable and can be used as a separate stand-alone unit, because each storage compartment is equipped with a wireless transceiver 180 to report back the status of each medication bottle 110 to the main medication tray 100. Storage compartment 140 includes a weight scale 160 unit used to measure and monitor the weight of the medication being stored in that storage compartment 140. Additionally, each weight scale unit 160 may further include a sensor unit 170 to indicate when medication containers 110 have been placed into and removed from the storage compartment 140. It can be seen in FIG. 2B a medication container 110 being placed inside the storage compartment 140.

Figure 3A:
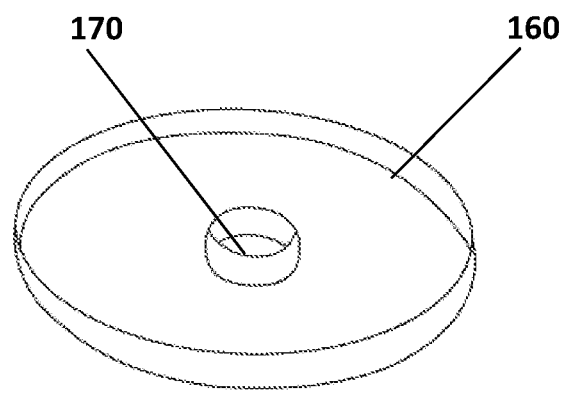
FIG. 3A is a detail of a medication weight scale and sensor unit of the present invention.
Figure 3B:
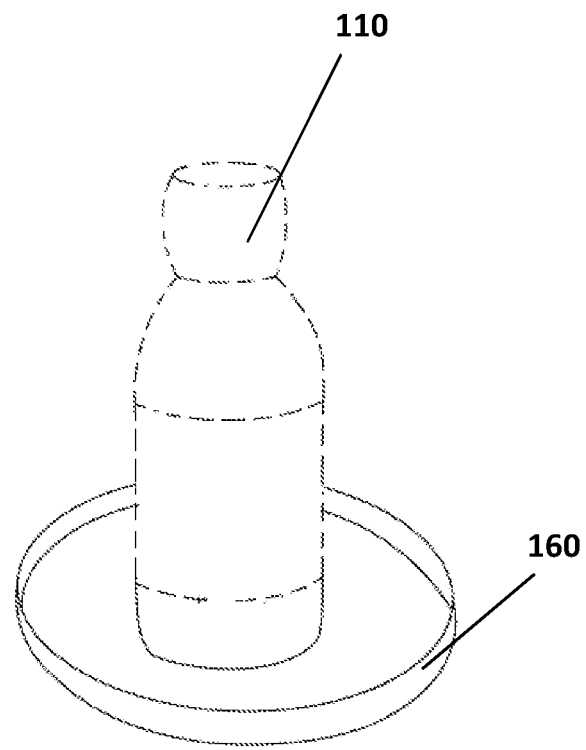
FIG. 3B is a detail of a medication weight scale and sensor unit of the present invention shown in use with a medication container.

Referring now to FIGS. 3A and 3B, there is shown a detail of the weight scale 160 and sensor 170 of the present invention. As can be seen, one of the novel features of the present invention is that each storage compartment 140 can further be used as a separate stand-alone unit, equipped with wireless transceiver 180 to report the status of each medication bottle 110 to the main medication tray 100. As shown in FIG. 3B, when a medication container 110 is placed inside a storage compartment 140, it is also being placed on the weight scale 160.

Figure 4:
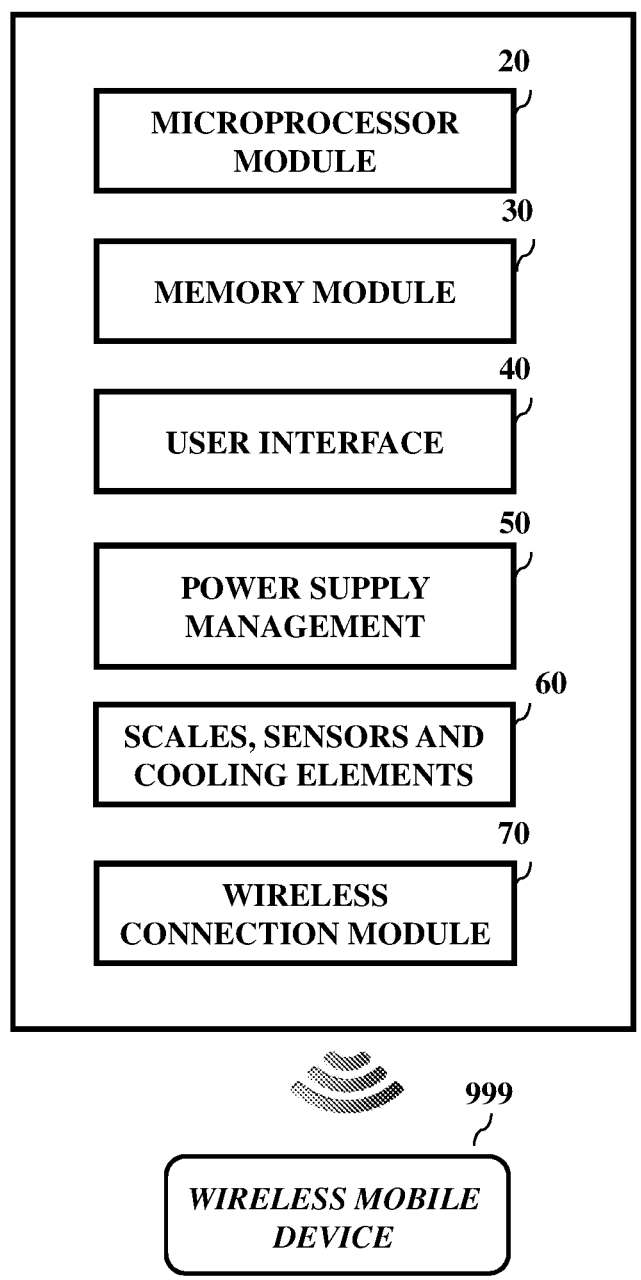
FIG. 4 is an illustration of the hardware structure of the present invention.

Referring now to FIG. 4, there is shown the overall hardware structure 2000 of the present invention. The hardware structure 2000 includes a microprocessor module 20, a memory module 30, a user interface 40, a power supply management module 50, a scales, sensors and cooling elements module 60, a wireless communications module 70 and a wireless device 999.

Figure 5:
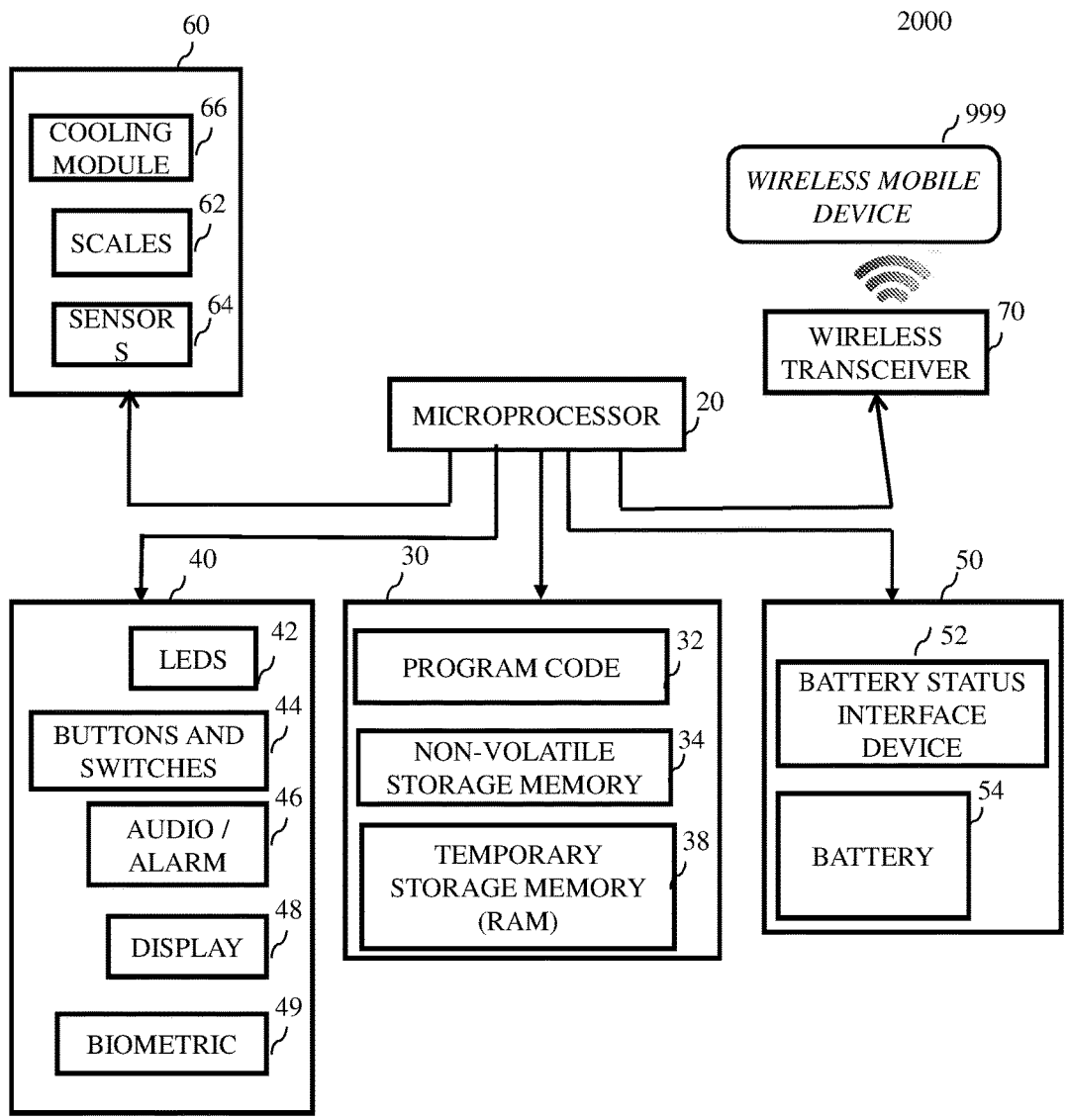
FIG. 5 is a hardware flow diagram of the hardware structure of the present invention.

The hardware structure 2000 is shown in detail in FIG. 5, wherein a wireless device 999 can be paired with the present invention, in order to interactively provide information on the medication being stored on the device as well as adherence updates process to the wireless device 999. The hardware architecture 2000 is contained within an appropriate housing, an example of one such embodiment is shown in FIG. 1. The present invention 1000 includes a microprocessor 20 that provides the computing power, a wireless transceiver 70 that communicates with the outside wireless device 999 via telemetry. User interface module 40 of the current invention 100 includes a display unit 48 for viewing various prompts and messages. User interface module 40 also includes a plurality of buttons and switches 44, an audio device 46 to prompt the operator. User interface module 40 also includes a biometric reader 49 to securely identify an authorized user of the present invention 1000. A number of light emitting diodes (LEDs) 42 will also provide the operator with visual feedback of the status. Battery power management 50 contains a rechargeable battery 54 that provides the power source 50 for the present invention 1000, and the supporting circuitry 52 provides feedback to the status of the battery-charge available. Memory module 30, provides storage area for the internal programming, as well as storing various information related to the patient and each medication container 110. Scales and sensors module 60 include scales 62, sensors 64 and cooling module 66, all of which combine to provide information on the presence of medication containers 110 in each storage compartment 140 as well as feedback on the amount of medication available in each medication container 110.

Referring now to FIGS. 4 and 5, the present invention SMART Medication Adherence Tray 1000 has a hardware flow control 2000. Wireless transceiver 70 will communicate with the outside wireless device 999 via telemetry and pairs with the wireless device. Audio alarm 46, Status LEDs 42 and display unit 48 provide audio and visual indication of the status of the pairing process as well as information related to the patient along information on each medication container. Sensors 64 provide feedback on the presence of medication containers in each storage compartment. Scales 62 is utilized to measure the weight of each container bottle being stored in the storage compartments, in order to provide detail data on each medication usage along with the amount and the time the medication was used by the patient, therefore assisting with the adherence monitoring process. Microprocessor 20 saves various data related to the patent along with prescription information and details on each medication container in the primary memory 34. Biometric sensing module 49 is utilized to authenticate authorized users access to the Smart Medication Adherence Tray 100.

The present invention 100 further utilizes a wireless communication module for interaction with outside computing devices and operators. Furthermore, the present invention 100 further utilizes local USB ports as well as various wireless means including but not limited Bluetooth, WiFi, 2G/3G communication to download prescriptions as well as instructional Text, Images and Videos related to the medication containers 100 into its onboard storage memory.

Figure 6:
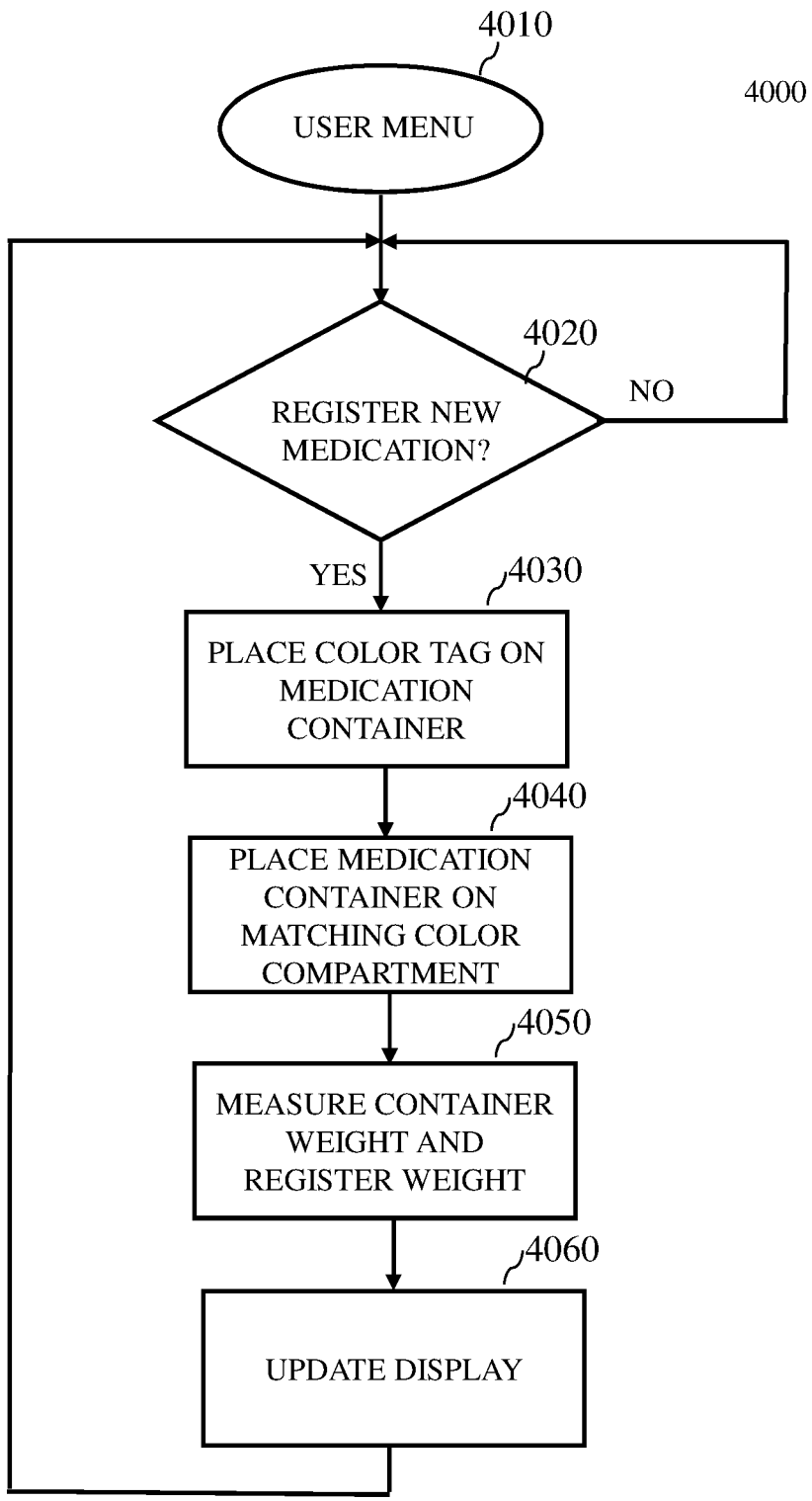
FIG. 6 is a process diagram of a registration of new medication container of the present invention.

Referring now to FIG. 6, there is shown the process of entering or registering a color-coding 4000 to a medication bottle into the present invention 1000. New medication bottle may be scanned with built-in or attachable bar-code scanner or may be entered manually. The User menu 4010 will allow a user to enter or register 4020 the details of a new medication, such as name of medication, dosage, times when the medication is to be taken. Optionally, at step 4030, a color tag will be associated with the medication. This color tag will be reflected in the user interface 150, which if color, will display this color whenever discussing this medication, will assign a storage compartment 140 having this color to this medication container 110, and will reference this color to the user during reminders and updates. At the next step 4040, the medication container 110 is placed in the storage compartment 140, with the optional matching color, and the medication container 110 is weighed and the weight of the medication container 110 is then registered and logged for future reference. At 4060, the display or user interface 150 is updated, reflecting this information.

Figure 7:
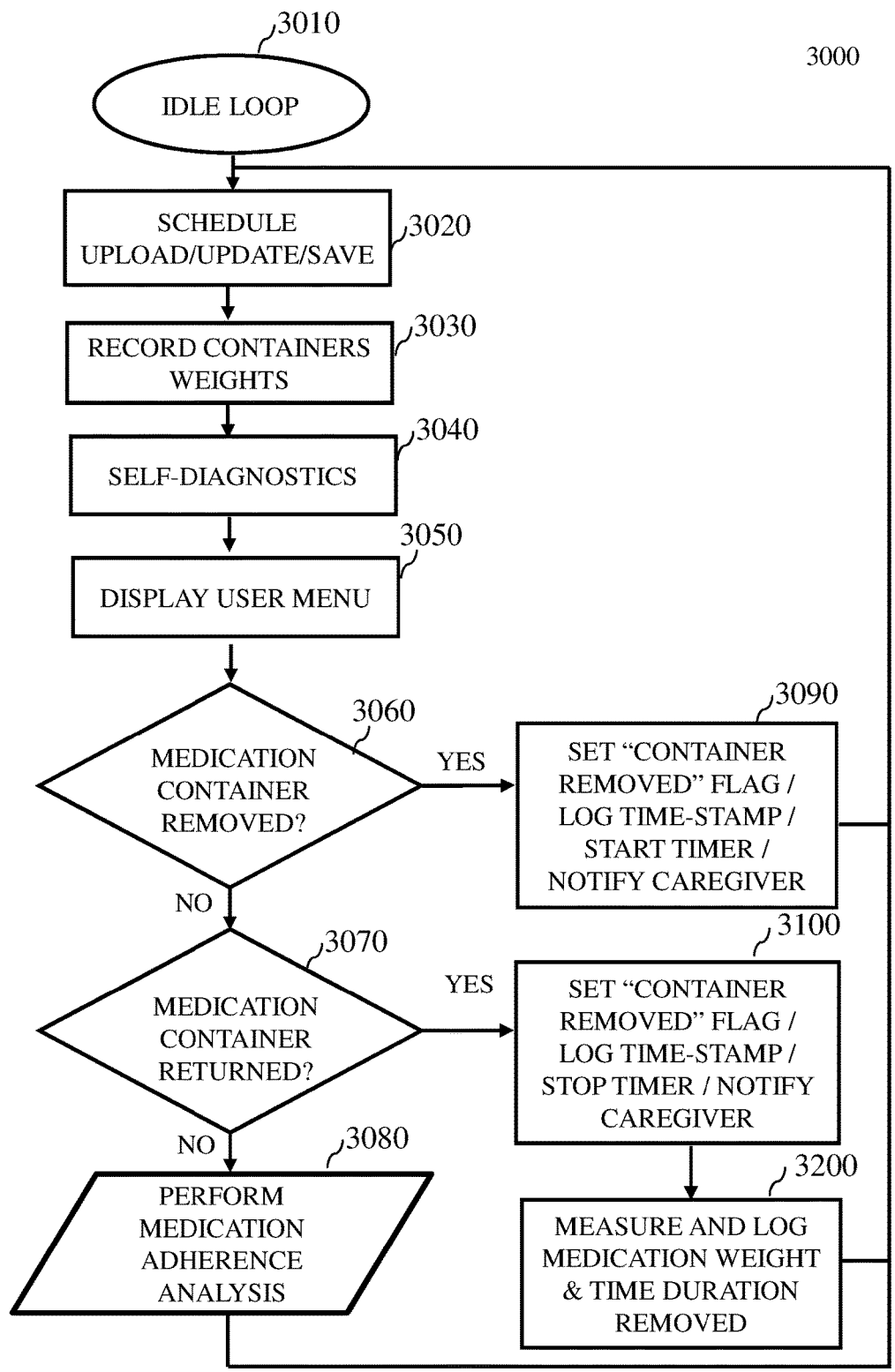
FIG. 7 is a process diagram of a container monitoring structure of the present invention.

Referring now to FIG. 7, there is shown the logic flow of the process diagram of a container monitoring structure 3000 of the present invention 1000. With the system running at 3010, the system monitors or detects if it is time to upload, update, or save any data, at 3020. At 3030, the system automatically weighs and records the weight of each of the medication containers 110 in the storage compartments 140, the weight of the storage compartment 140 is already known and accounted for in the calculations. Preferably, each storage compartment 140 has only one medication container 110 in it. As discussed above, each storage compartment 140 may be color-coded. At 3040, the present invention performs a self-diagnostic, then activates and displays the user menu and interface 150 at step 3050. At 3060, the present invention senses whether a medication container 110 has been removed from the storage compartment 140. Optionally, the user interface 150 may request a prompt directly from the user. If a medication container 110 has been removed, then at 3090, a flag that the container has been removed is set, a timer starts to record how long the medication container 110 is away from the storage compartment 140, and a notice is sent to the caregiver, whether remote or nearby. Once all these are complete, the system returns to 3020 and performs the steps through 3060 where it awaits to sense and detect that the medication container 110 has been returned to the storage container 140 at 3070. If the present invention does detect that the medication 110 has been returned to the storage compartment 150 at 3070, then at 3100 the "container removed" flag is reset, the timer is stopped, the time of the return is noted and logged, the timer is reset, and the caregiver or user is notified. This is followed by 3110, where the medication container 110 is weighed and the new weight is logged as well as the duration of time the medication was away from the storage compartment. At the same time, at 3080, the present invention performs its analysis on the medication adherence process, by comparing the weight of medication used to the previously entered required dosage, and by checking the time stamp and checking the previously entered medication times, and further by reporting how closely to these required factors the patient is maintaining or adhering to a medication program. The present invention will then report this information to the user and optionally to a remote caregiver. The present invention then returns to 3020 to continuously check the medication usage.

Figure 8:
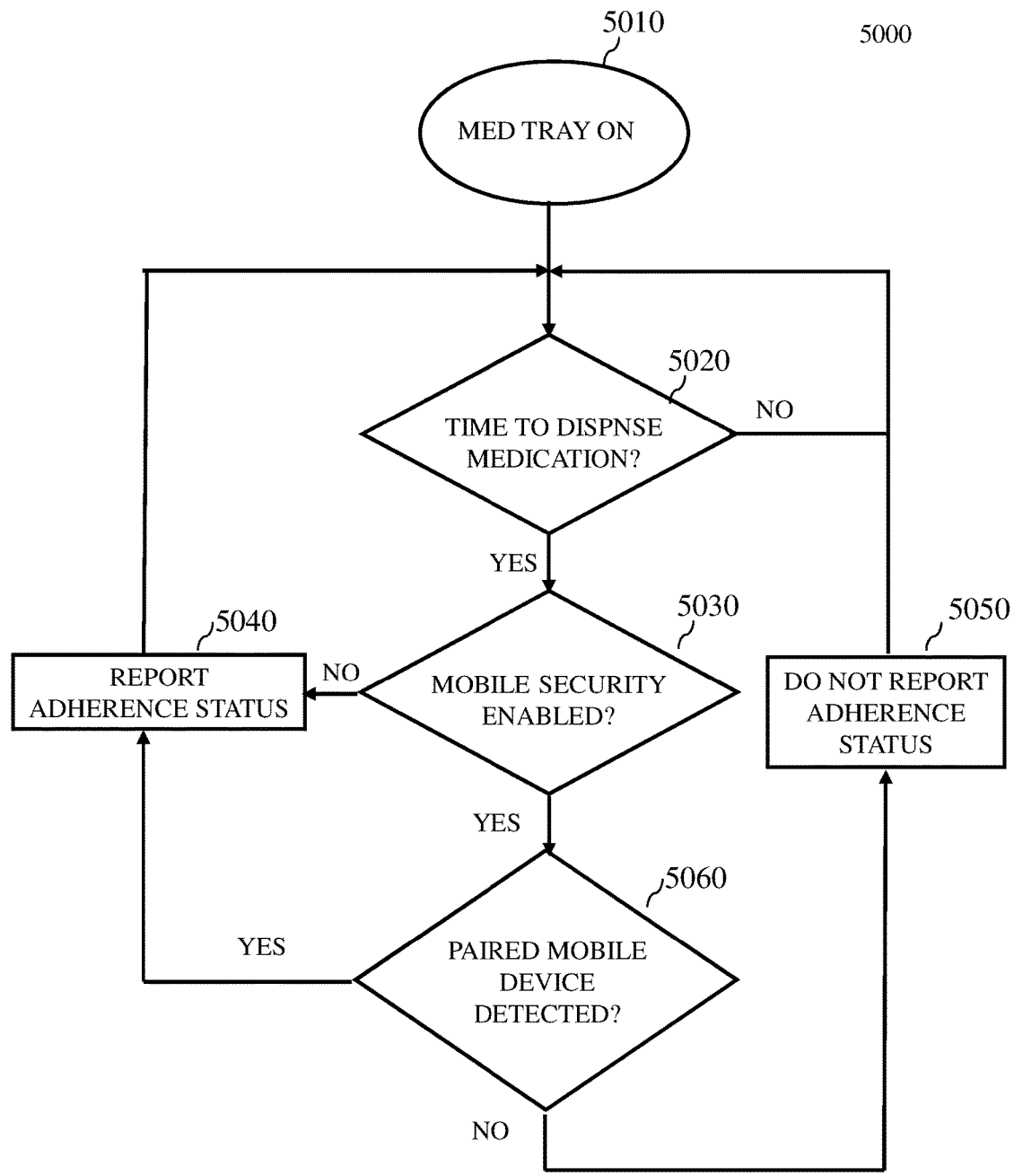
FIG. 8 is a process diagram of a mobile security system of the present invention.

Referring now to FIG. 8, there is shown the security protocol 5000 of the present invention 1000. This protocol will send the medication adherence status to a mobile device that is registered and paired with the present invention. An example is the patient is using an app on a mobile device that is run in conjunction with the present invention. Optionally this protocol may be used for other purposes, such as sending a notification if an unauthorized user is using the medication. Another option is to notify caregivers if an unauthorized person is using the medication. An unauthorized user is one who does not have a mobile security device that is registered with the present invention. The present invention medical tray's system is on, 5010. It monitors and continuously checks, at 5020, whether it is time, according to previously entered schedule, for the patient to take medication. When 5020 determines that it is time for medication to be dispensed, 5030 checks to see if mobile security of the present invention is enabled. If not, it reports the medication adherence status as usual at 5040. If the mobile security feature at 5030 is enabled, the next step, 5060, checks to see if a paired mobile device is detected. If a paired mobile device is not detected, then the present invention will not report the adherence status, 5050. If a paired mobile device is detected then a report on the adherence status will be sent 5040. This requires the user to carry the mobile device with them to authenticate the appropriate user is taking the medication.

Figure 9A:
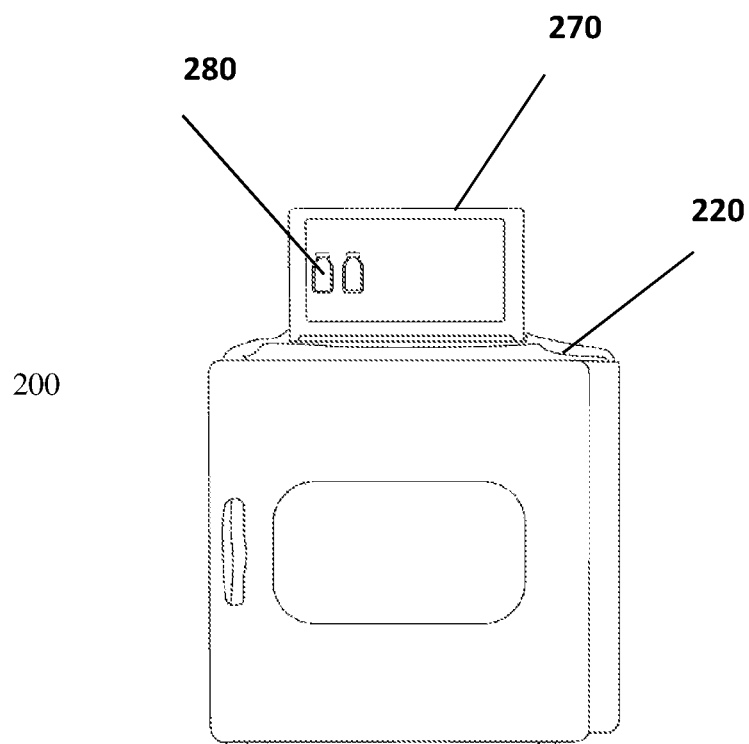
FIG. 9A is a second embodiment of the present invention, shown in the closed position and with the user interface upright.
Figure 9B:
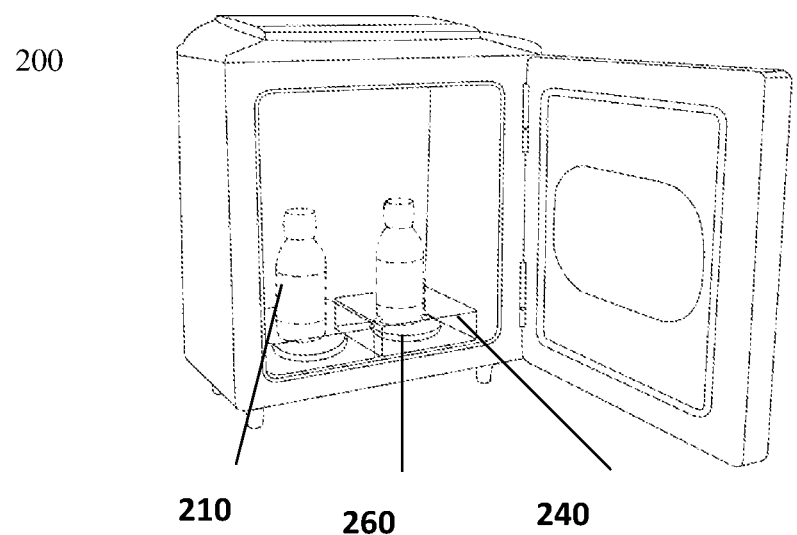
FIG. 9B is a second embodiment of the present invention, shown in the open position and with the user interface down.
Figure 10:
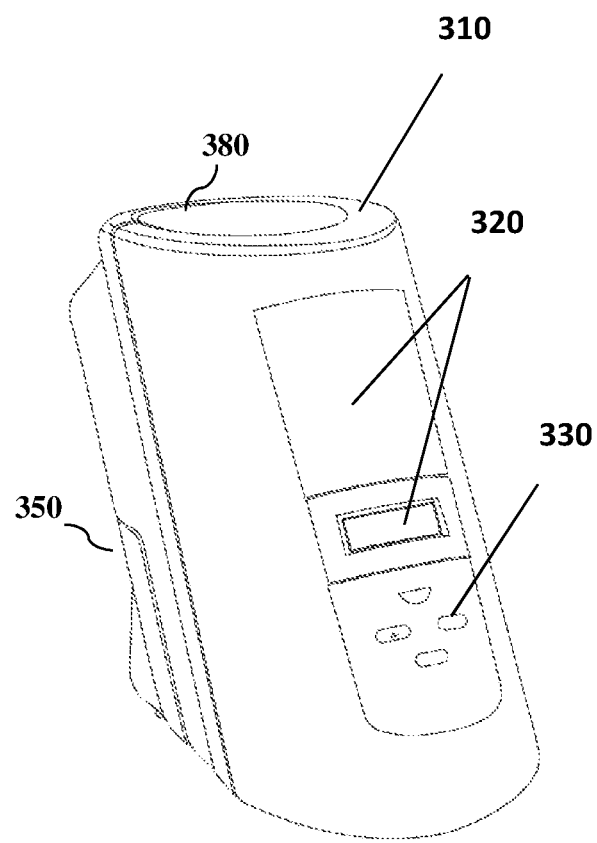
FIG. 10 is a third embodiment of the present invention, shown in the closed position.

Referring now to FIGS. 9A and 9B, there is shown a second embodiment 200 of the Smart Medication Adherence Refrigeration Tray (SMART) capable of providing cooling mechanism for the stored medication 210. A display unit 270, including but not limited to a mobile device or tablet computer will display 280 the available contents in each medication container 210. Medication bottles 210 are placed in the storage compartments 240 of the Medication Tray 200. Each medication storage compartment 240 includes a weight scale 260 unit used to measure and monitor the weight of the medication being stored in that storage compartment 240.

Figure 11A:
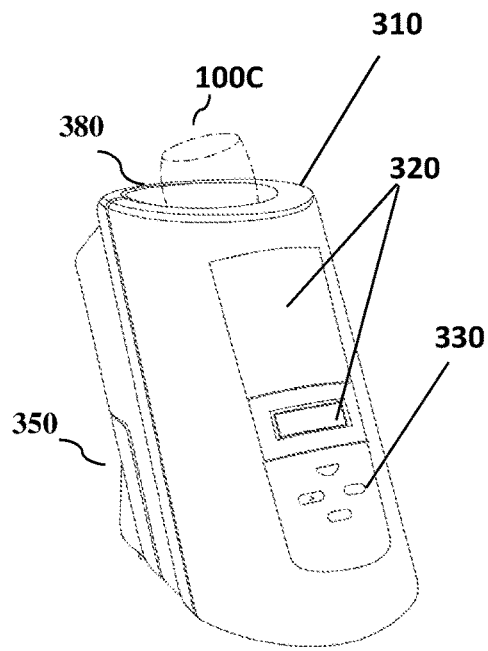
FIG. 11A is a third embodiment of the present invention, shown in the closed position and in use with a medication container.
Figure 11B:
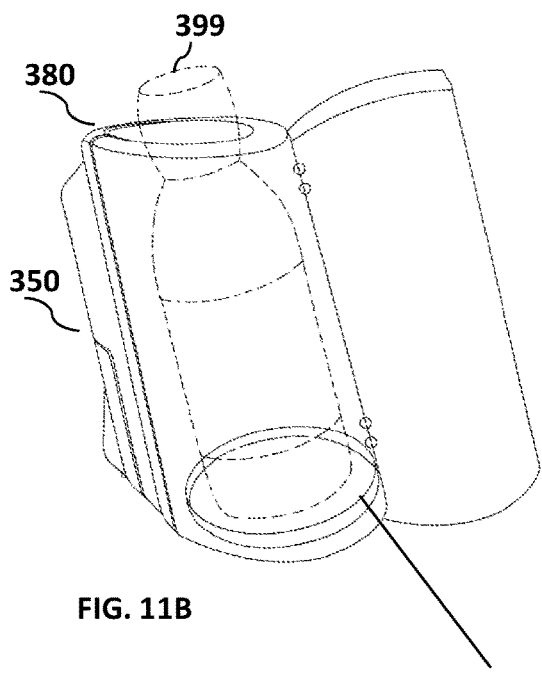
FIG. 11B is a third embodiment of the present invention, shown in the open position and in use with a medication container.
Figure 11C:
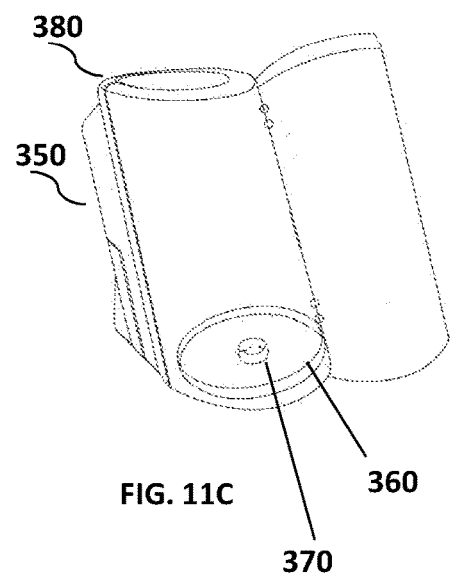
FIG. 11C is a third embodiment of the present invention, shown in the open position and in use with a small medication container.

Referring now to FIGS. 10, 11A-11C, there is shown a third embodiment 300 of the Smart Medication Adherence Refrigeration Tray (SMART) capable of providing cooling mechanism for the stored medication 399. One or more display unit 320 and buttons 330 for interacting with the operator. A housing 310 further includes a self-contained cooling mechanism 350 to maintain optimal temperature of the medication placed therein. The housing 310 provides an opening 380 for the top of the medication container 399 if the medication container 399 is large, as shown in FIG. 11B. It can also be seen in FIG. 11C that the present invention 300 further accommodates smaller medication containers 399. A door 340 allows access to the medication 399. Medication container 399 is placed inside the housing 310 on the Weight scale 360 containing the sensor 370.

One of the unique and novel features of the present invention is that it can remind a user or caregiver that a medication is running low, needs to be refilled, has expired, or if the user is not supposed to take the medication any longer. A user and caregiver can then refill the medication in time to prevent missing a dosage and the present invention can also notify the caregiver to prevent the user from taking medication that the patient no longer needs.

Additionally, another unique and novel feature of the present invention is that patients often get confused with all the different medication times. Some medications taking instructions include: one a day, twice a day, three times a day, four times a day, before a meal, with breakfast, with lunch, with dinner, with food, after a meal, before exercise, before bed. Keeping track of all these time requirements is confusing and imprecise. The present invention keeps track of all these times and reminds the patient user and caregiver, which medication is to be taken at the appropriate time. The present invention can even handle those medications that are to be dosed out "as needed," reporting the need to the caregiver and keeping track of these medications.

Another unique and novel feature of the present invention is that a report of the medication adherence status can be provided to a doctor and become part of the patient's medical record or as a support for a caregiver in reviewing the needs for future or continuing care.

One of the unique and novel features of the present invention is that it can provide information as to whether a medication has or has not been taken. For example, a user may not remember if a medication has been taken and therefore may inadvertently take a second dose. The present invention can provide information to the user and the care giver to prevent the additional dose or to immediately notify a caregiver if an extra dose was taken.

One of the unique and novel abilities of the present invention its ability to help patients, and caregivers maintain a prescribed medication regimen. These include:
  a. New bottle is scanned with built-in or attachable bar-code scanner;
  b. Placed in one of the storage compartments;
  c. Its initial weight measured and logged;
  d. Each time bottle is removed, sensor can notify caregiver remotely of the event (if this option is enabled);
  e. When bottle is returned, sensor can notify the caregiver;
  f. The weight is re-measured and logged;
  g. Weight is compared to proviso logged weight to calculate usage;
  h. Usage is reported to Caregiver/User;
  i. Usage is compared to pre-stored medication prescription schedule;
  j. Caregiver/User r is notified of compliance or not;
  k. Color coded medication slots;
  l. Color match sensor assuring medication is taken and returned to its proper slot;
  m. GPS location of tray for remote assurance that the tray is with the user-proximity measurement to the hub; and
  n. Optionally, Medication distance alarm from Hub (in case of travel, reminds to take the medication tray from the fridge.

Another unique and novel ability of the present invention is its ability to create a medication adherence report, giving very detailed information to a caregiver, and the user, as to how closely the patient is following its medication regime and also to ensure that medication that needs to be refrigerated is returned to a cooling unit. Included are:
  a. Each time bottle is removed, a timer starts for that particular medication;
  b. When bottle is returned, the timer stops and logs the amount of time bottle was left out of the unit (and possibly refrigeration);
  c. Logs and compares the dosage taken vs. prescribed for a potential alert to the user/caregiver; and
  d. If bottle is not returned within pre-scheduled allowable time, Caregiver/User is alerted.

Another unique and novel feature is the real-time reporting and monitoring and interactiveness of the present invention. This includes a Caregiver/User downloads to the device the medication prescription, usage schedule, dosage amount, location of medication (such as refrigerator, freezer, etc.), and alert information (such as email addresses, phone numbers, etc.). The Schedule is saved in on-board non-volatile memory. Wireless communication is used to alert outside Caregiver/User is alerted.

Another unique and novel feature of the present invention is an optional Thermistor provided on the present invention medication tray 100. This provides that if tray 100 or storage container 140 temperature drops below allowable range (unit is outside fridge for too long), Caregiver/User is notified.

Another unique and novel feature of the present invention is a color-coding of the medication 110 and the storage compartment 140. This will provide for the medication to also be referenced by color rather than by name and the color will appear on the storage compartment 140 and on the user interface 150. An example is that a patient can see that it is time to take the purple medication, or the present invention can tell the user that the medication was returned to the red compartment rather than the purple compartment, and the like. This includes:
  a. Color Coding of Medication bottles along with storage components concept
  b. Color-coded tags placed on each bottle
  c. Matching color-coded storage components This feature is particularly useful for a user that is of age where there is difficulty reading the labels is able to access the medication fast, none time or effort consuming and thus adheres better to the prescribed regiment.

Another unique and novel feature of the present invention is that the present invention can embody a self-contained, built-in, cooling compartment. This has the advantage of providing medication that needs refrigeration while a user is traveling or at the bedside without the need for ice or a refrigerator. This feature has the further benefit of preventing the spoilage of medications. Some medicines require special storage conditions such as in the refrigerator, or even the freezer. Such medicines can expire quickly if they are improperly stored at room temperature, becoming toxic or less effective. The present invention prevents this by providing the cooling unit. In some cases, the medication need not be removed from the cooling unit and the medication can be accessed directly.

Another unique and novel feature of the present invention is that the storage compartments 140 can be removable. In addition to that the storage compartments 140 may be in wireless communication, such as Bluetooth, with the base tray. In another embodiment the storage compartments 140 may be in RFID communication with the base tray 100 to verify and authenticate user adherence. By detaching the color coded compartment 140 and having it transmit to the box base 100, the present invention assures that the medication container 110 will be returned to the storage compartment 140 with minimal to no chance of medication container 110 (aerosol/liquid and etc) confusion.

Another unique and novel feature of the present invention is the Mobile Device Authentication/Security feature. The present invention notifies the Caregiver/User if a paired mobile device is within close proximity of the present invention 100 (or its detachable storage component 140) when bottle 110 is removed, Other unique and novel features of the present invention include:
  a. Built-in sensor to detect when bottle is removed and when placed back;
  b. Built-in scale to indicate how much medication was taken out;
  c. Interactive Analog Monitoring of Medication use (Apparatus & Process);
  d. Secure Mobile Access, if enabled, flags remote operator if bottle was removed when Mobile device was not near by;
  e. Expandable tray, to support one or more medication containers
  f. Tray extension slides out
  g. Tray extension unfolds (similar to airplane trays)
  h. Removable wireless-enabled medication holders/trays with built-in scale
  i. Stand-alone bottle holder (Tray) with built-in thermo-electric cooler, scale, sensor and wireless
  j. Built-in Barcode reader to register medication bottles, track and report them

What is claimed is:
1. A medication-adherence assistance apparatus to provide assistance maintaining a medication regimen, to remind a user to take medication, to provide information to users, operators, and caregivers, and to track medication compliance, said users, operators, and caregivers, and the user having at least one medication container containing a medication and the medication having a dosage and a schedule, the apparatus comprising:

a. a processor;
b. a memory;
c. a wireless transceiver, wherein said wireless transceiver may include a multiplicity of functions, including downloading and providing access to a medication schedule and medication dosage;
d. a speaker;
e. an interface, the interface further comprising a display and at least one input device;
f. at least one storage compartment for placing and storing the medication container, the at least one storage compartment having a base, and the at least one storage compartment being associated with a single medication container;
g. a scale mechanism;
h. a sensor mechanism;
i. a housing, said housing configured to contain the processor, the memory, the wireless transceiver, the display, the speaker, the sensor mechanism, and the at least one storage compartment;
j. wherein said wireless transceiver, said scale and said sensor reside on the base of the storage compartment and are in electronic communication with each other wherein said transceiver, scale, and sensor detect when medication has been removed from the base as well as when medication has been returned to the base, notify remote operators and caregivers when medication is dispensed, detect the weight of each medication container at all times and log the weight information prior to each time a bottle is removed and immediately after the bottle is returned, calculate the amount of medication being used each time, providing notifications to a user via the interface display and the speaker, and notify remote operators and caregivers;
k. a dispense schedule, wherein said dispense schedule is downloaded into the device, remotely or locally, and wherein said dispense schedule further is capable of receiving the dosage of the medication;
l. a monitoring protocol, wherein said monitoring protocol monitors the downloaded medication schedule and wirelessly notifies local operators and remote operators and caregivers of when the medication container has been removed from and returned to the storage compartment of the tray, and the amount of medication that was used; and
m. wherein the device, programs, and protocols are capable of being programmed with the medication dosage and usage schedule for one or more medication containers.

2. The medication-adherence assistance apparatus of claim 1, wherein the apparatus further comprises a microphone.

3. The medication-adherence assistance apparatus of claim 1, wherein the at least one storage compartment is removable from the housing.

4. The medication-adherence assistance apparatus of claim 3, wherein the apparatus further comprises a time out alert, wherein the apparatus, upon sensing when a storage compartment has been removed from the housing, begins a timer of a predetermined length of time, at the end of which the interface display and speaker provide notifications to the user to return the storage compartment to the housing.

5. The medication-adherence assistance apparatus of claim 3, wherein the apparatus further comprises a time out alert, wherein the apparatus, upon sensing when a storage compartment has been removed from the housing, begins a timer of a predetermined length of time, at the end of which the interface display and speaker provide notifications to remote operators and care givers that the storage compartment has not been returned to the housing.

6. The medication-adherence assistance apparatus of claim 1, wherein the apparatus further comprises a color-coded system, wherein the storage compartment is designated a color and the programs, protocols and display unit further record and report the color coding in association with the medication and other reporting functions, and whereby each medication container is matched with an individual and designated storage compartment in the housing and shown on the interface.

7. The medication-adherence assistance apparatus of claim 6, wherein the color-coded system further comprises a specific location for each individual color-coded storage compartment and a sensor that can detect if a color-coded storage compartment has or has not been returned to the color-coded storage compartment's color-coded location, and an alert to notify the user to return the color-coded storage compartment to its designated location.

8. The medication-adherence assistance apparatus of claim 1, wherein the apparatus further comprises a cooling mechanism and housing that encompasses the storage compartment and its associated medication container providing that medications that require refrigeration are kept cool while outside of a refrigerator.

9. The medication-adherence assistance apparatus of claim 1, wherein the at least one storage compartment is removable and further comprises a wireless connectivity link to the main medication housing.

10. The medication-adherence assistance apparatus of claim 1, wherein the apparatus further comprises a GPS locator to notify remote operators and care givers via wireless communication of the location of the device.

11. The medication-adherence assistance apparatus of claim 1, wherein the apparatus further comprises a bar-code scanner to scan in medication containers.

12. The medication-adherence assistance apparatus of claim 1, wherein the apparatus further comprises an alarm to remind the user to take medication and to remind the user to return the storage compartment to a refrigerator.

13. The medication-adherence assistance apparatus of claim 1, wherein the housing further comprises a self-contained cooling compartment.

14. The medication-adherence assistance apparatus of claim 1, wherein the apparatus further comprises a secure mobile access, wherein the apparatus is paired to a wireless device and notifies the caregiver and user of the user's medication-adherence status.

15. The medication-adherence assistance apparatus of claim 1, wherein the at least one storage compartment is a removable stand-alone storage compartment configured to detect when a medication bottle is removed from and returned to a storage container, to log that information, to compare the information with pre-stored medication usage schedule, and to report that information via wireless communication to the apparatus and to an operator user.

16. The medication-adherence assistance apparatus of claim 15, wherein the removable stand-alone storage compartment is further configured to determine the weight of the medication container before the medication container is removed from container and after when it is returned, to log that information, to compare the information with pre-stored medication usage schedule, and to report that information via wireless communication to the apparatus and to an operator user.

17. The medication-adherence assistance apparatus of claim 15, wherein the removable stand-alone storage compartments further comprises a GPS locator device configured to monitor the location of the medication container and to notify remote operators and caregivers via wireless communication of the location of the device.

18. The medication-adherence assistance apparatus of claim 1, wherein the housing is generally a tray.

19. A method of medication-adherence assistance to provide assistance maintaining a medication regimen, to remind a user to take medication, to provide information to users, operators, and caregivers, and to track medication compliance, said users, operators, and caregivers, and the user having at least one medication container containing a medication and the medication having a dosage and a schedule, the method comprising the steps of:
   a. entering a new medication container's data, at least including, name of medication, dosage, medication schedule and storing the entered information;
   b. placing the medication container in a storage compartment;
   c. weighing the medication container and logging that data;
   d. notifying a caregiver remotely that a medication container was placed in a storage compartment;
   e. sensing when a medication container is removed from the storage compartment;
   f. sensing when a medication container is returned to the storage compartment;
   g. weighing the medication container and logging the data;
   h. comparing weight of the medication container after Mal the medication container was used and returned to the previously logged weight and calculating the weight of medication used;
   i. reporting to the caregiver remotely the amount of medication used;
   j. comparing the amount of medication used to the previously stored required dosage information;
   k. determining if the amount of medication used was in compliance with the required dosage; and
   l. notifying the caregiver whether or not the amount of medication taken was in compliance with the required dosage.

20. The method of claim 19, further comprising the steps of a color-coding matching protocol comprising the steps of:
   m. color-coding the storage compartments;
   n. color-coding each storage compartment's designated location in the housing tray;
   o. sensing whether the color-coded storage compartment is residing on the color-coded storage compartment's designated location;
   p. notifying the user when the color-coded storage compartment is not residing on the color-coded storage compartment's designated location; and
   q. continuing the notification until the color-coded storage compartment is placed in the color-coded storage compartment's designated location.

21. The method of claim 19, further comprising the steps of a color-coded notification protocol comprising the steps of:
   r. affixing a color-coded tag on the medication container;
   s. placing the tagged medication container in a storage compartment having the same color as the tag; and
   t. displaying the color on a user interface when referencing the medication.

22. The method of claim 19, further comprising a the steps of a GPS locator protocol comprising the steps of:
   u. adding a GPS locator to the housing tray; and
   v. accessing the GPS locator, for a user to find a missing tray and for a remote caregiver to assure that tray is with the user and within proximity to the tray's hub.

23. The method of claim 22, further comprising the steps of
   w. sensing how long a storage compartment has been away from a refrigerator; and
   x. notifying the user to return the storage compartment to the refrigerator.

24. The method of claim 19, further comprising the steps of a mobile device security protocol comprising the steps of:
   y. waiting and sensing that in accordance with the medical schedule, the appropriate time is occurring for medication to be dispensed;
   z. sensing whether a mobile security device is within connectivity range;
   aa. notifying the user to take medication, if no mobile security device is detected nearby;
   bb. returning to step z until a mobile security device is detected;
   cc. detecting whether the mobile security device is enabled;
   dd. notifying the user of the medication adherence status; and
   ee. returning to the beginning of this loop.

25. The method of claim 19, further comprising the steps of a mobile security adherence protocol comprising the steps of:
   cc. notifying a remote caregiver that in accordance with the medical schedule, the time to take medication is occurring, if no mobile security device is detected nearby; and
   dd. notifying a remote caregiver of the medication adherence status.

26. The method of claim 19, further comprising the steps of a mobile security adherence protocol comprising the steps of:
   a. notifying a remote caregiver in accordance with the medical schedule, the time to take medication is occurring, if no mobile security device is detected nearby; and
   b. notifying a remote caregiver of the medication adherence status.

27. A method of medication-adherence assistance to provide assistance maintaining a medication regimen, to remind a user to take medication, to provide information to users, operators, and caregivers, and to track medication compliance, said users, operators, and caregivers, and the user having at least one medication container containing a medication and the medication having a dosage and a schedule, and further provided with a storage container and a display unit, the method comprising the steps of:
   a. receiving, uploading, updating and saving medication information, including name of medication, dosage, and dosage schedule;
   b. performing self-diagnostics;
   c. weighing the medication container and recording the weight;
   d. sensing whether the medication container has been removed from a storage container;

e. logging the time stamp of the removal of a medication container from a storage container, starting a timer, and notifying a caregiver;

f. sensing whether the medication container has been returned to the storage container;

g. logging the time stamp or the return of the medication container to the storage tray, stopping the timer, and notifying a caregiver;

h. weighing and logging the weight of the returned medication container and the duration of time the medication container was removed from the storage container;

i. perform medication adherence analysis, said adherence analysis further comprising the steps of comparing the weight of the medication used to the amount of the previously entered dosage, comparing the time stamp when the medication was removed to the previously entered dosage schedule; and j. reporting the data from the medication adherence analysis to the user.

28. The method of claim 27, further comprising the step of reporting the results to a remote caregiver.

29. The method of claim 27, further comprising the step of sending the notifications via a display unit.

30. The method of claim 27, further comprising the step of sending the notifications via wireless devices.

31. The method of claim 27, further comprising the step of associating the medication container with a particular storage compartment.

32. The method of claim 27, further comprising the steps of a color-coding matching protocol comprising the steps of:

a. color-coding the storage compartments;

b. color-coding each storage compartment's designated location in the housing tray;

c. sensing whether the color-coded storage compartment is residing on the color-coded storage compartment's designated location;

d. notifying the user when the color-coded storage compartment is not residing on the color-coded storage compartment's designated location; and e. continuing the notification until the color-coded storage compartment is placed in the color-coded storage compartment's designated location.

33. The method of claim 27, further comprising the steps of a color-coded notification protocol comprising the steps of:

a. affixing a color-coded tag on the medication container;

b. placing the tagged medication container in a storage compartment having the same color as the tag; and c. displaying the color on a user interface when referencing the medication.

34. The method of claim 27, further comprising a the steps of a GPS locator protocol comprising the steps of:

a. adding a GPS locator to the housing tray; and b. accessing the GPS locator and locating a missing tray, and assuring a remote caregiver that tray is with the user and within proximity to the tray's hub.

35. The method of claim 34, further comprising the steps of a. sensing how long a storage compartment has been away from a refrigerator; and b. notifying the user to return the storage compartment to the refrigerator.

36. The method of claim 27, further comprising the steps of a mobile device security protocol comprising the steps of:

a. waiting and sensing the appropriate time for medication to be dispensed;

b. sensing whether a mobile security device is within connectivity range;

c. notifying the user in accordance with the medical schedule, the time to take medication is occurring, if no mobile security device is detected nearby;

d. returning to step z until a mobile security device is detected;

e. detecting whether the mobile security device is enabled;

f. notifying the user of the medication adherence status; and g. returning to the beginning of this loop.

\* \* \* \* \*